US009188524B2

(12) United States Patent
Yamasaki

(10) Patent No.: US 9,188,524 B2
(45) Date of Patent: Nov. 17, 2015

(54) PARTICLE DETECTING SYSTEM AND PARTICLE DETECTING METHOD

(71) Applicant: Azbil Corporation, Tokyo (JP)

(72) Inventor: Shinsuke Yamasaki, Tokyo (JP)

(73) Assignee: AZBIL CORPORATION, Tokyo (JP)

( * ) Notice: Subject to any disclaimer, the term of this patent is extended or adjusted under 35 U.S.C. 154(b) by 2 days.

(21) Appl. No.: 14/178,733

(22) Filed: Feb. 12, 2014

(65) Prior Publication Data

US 2014/0225005 A1     Aug. 14, 2014

(30) Foreign Application Priority Data

Feb. 12, 2013   (JP) .................................. 2013-024635

(51) Int. Cl.
*G01N 33/49*     (2006.01)
*G01N 15/14*     (2006.01)
*G01N 15/00*     (2006.01)

(52) U.S. Cl.
CPC .... *G01N 15/1459* (2013.01); *G01N 2015/0046* (2013.01)

(58) Field of Classification Search
CPC ... G01N 15/0205; G01N 15/02; G01N 15/14; G01N 2015/1236
USPC ................... 250/459.1, 458.1, 573, 435, 397; 356/336, 337, 338, 335
See application file for complete search history.

(56) References Cited

U.S. PATENT DOCUMENTS

| 5,006,227 | A | * | 4/1991 | Behm et al. .................. 209/143 |
| 6,885,440 | B2 | | 4/2005 | Silcott et al. |
| 7,106,442 | B2 | | 9/2006 | Silcott et al. |
| 8,358,411 | B2 | | 1/2013 | Babico et al. |
| 8,576,395 | B2 | | 11/2013 | Babico et al. |
| 2004/0050756 | A1 | * | 3/2004 | Flagan ........................... 209/156 |
| 2006/0079000 | A1 | * | 4/2006 | Floriano et al. ............... 436/164 |
| 2010/0000943 | A1 | * | 1/2010 | Carson et al. ................. 210/638 |
| 2011/0214489 | A1 | * | 9/2011 | Grant et al. ................... 73/61.72 |

(Continued)

FOREIGN PATENT DOCUMENTS

| JP | 2003-121315 A | 4/2003 |
| WO | 2010/080643 A1 | 7/2010 |

OTHER PUBLICATIONS

Venkatapathi, Murugesan et al., "High-speed Classification of Individual Bacterial Cells Using a Model-based Light Scatter System and Multivariate Statistics," Applied Optics, USA, Optical Society of America, Feb. 10, 2008, vol. 47, No. 5, pp. 678-686.

Sivaprakasam, Vasanthi et al., "Multiple UV Wavelength Excitation and Fluorescence of Bioaerosols," Optics Express, USA, Optical Society of America, Sep. 20, 2004, vol. 12, No. 19, pp. 4457-4466.

(Continued)

*Primary Examiner* — Marcus Taningco
*Assistant Examiner* — Djura Malevic
(74) *Attorney, Agent, or Firm* — Troutman Sanders LLP

(57) ABSTRACT

A particle detecting system includes an airborne particle detecting device that detects scattered light and/or fluorescent light produced through illuminating with light a particle included in a gas, a gas inspection flow path that introduces, into the airborne particle detecting device, a particle included in a gas that is subject to inspection, an aerosol generating portion that generates an aerosol from a liquid that is subject to inspection, and a liquids inspection flow path that introduces a particle included in the aerosol into the airborne particle detecting device.

10 Claims, 9 Drawing Sheets

(56) References Cited

U.S. PATENT DOCUMENTS

| | | | |
|---|---|---|---|
| 2011/0314937 A1* | 12/2011 | Johnson et al. | 73/863.22 |
| 2012/0174650 A1* | 7/2012 | Ariessohn et al. | 73/23.2 |
| 2012/0304671 A1* | 12/2012 | Hallett | 62/66 |
| 2014/0038277 A1 | 2/2014 | Babico et al. | |

OTHER PUBLICATIONS

Ross, et al., "The Water and Solid Content of Living Bacterial Spores and Vegetative Cells as Indicated by Refractive Index Measurements", J. gen. Microbiol. 16, 418-425.

* cited by examiner

Fluorescent Intensity (Grayscale Value per Individual Microorganism)

FIG. 8

PARTICLE DETECTING SYSTEM AND PARTICLE DETECTING METHOD

CROSS REFERENCE TO RELATED APPLICATION

This application claims priority under 35 U.S.C. §119 to Japanese Patent Application No. 2013-024635, filed on Feb. 12, 2013, the entire content of which being hereby incorporated herein by reference.

FIELD OF TECHNOLOGY

The present invention relates to an environment evaluating technology and, in particular, relates to a particle detecting system and a particle detecting method.

BACKGROUND

In fields such as pharmaceuticals, the electronics industry, semiconductor manufacturing, and the like, there is the need for high degrees of cleanliness with few contaminants such as airborne microorganism particles or non-microorganism particles in the air in the production environment. Airborne contamination can be broadly divided into insoluble contamination and soluble contamination. Moreover, in the manufacturing processes, there is the need for solutions or water with high degrees of cleanliness, from which contaminants have been removed.

For example, International Application Publication No. WO 2010/080643 ("the WO '643") describes a detecting device that discriminates between non-biological microparticles and biological microparticles included in an aerosol. Moreover, Japanese Unexamined Patent Application Publication No. 2003-121315 ("the JP '315"), for example, describes a method for counting particles in a liquid, using a liquid particle counter. In this method, a laser beam is directed at the medium to be measured, the intensity of scattered light is measured, and the intensity of scattered light is converted into a particle diameter, to thereby include counts, for each particle size, of the particles that exist in the medium being measured, using what is known as the "light scattering technique."

As described above, in a production environment that requires a high degree of cleanliness, the state of the air is inspected, and preferably is maintained in a state wherein there are few airborne particles. Moreover, in the liquids used in the manufacturing process as well, such as pure water, preferably the degree of purity is maintained. A particle detecting device, for use only with gases, such as described in the WO '643, and a particle detecting device used only with liquids, such as described in the JP '315, are used in parallel. Moreover, in the production environment, preferably the particles that are solids adhered to a clean bench, or the like, are also detected. Given this, an aspect of the present invention is to provide a particle detecting system and particle detecting method wherein it is possible to detect particles sampled from a plurality of locations using a single particle detecting device.

SUMMARY

The present invention provides a particle detecting system including: (a) an airborne particle detecting device for detecting scattered light and/or fluorescent light produced through illuminating with light a particle included in a gas; (b) a gas inspection flow path for introducing, into the airborne particle detecting device, a particle included in a gas that is subject to inspection; (c) an aerosol generating portion for generating an aerosol from a liquid that is subject to inspection; and (d) a liquids inspection flow path for introducing, into the airborne particle detecting device, a particle included in the aerosol.

The present invention provides a particle detecting system including: (a) an airborne particle detecting device for detecting scattered light and/or fluorescent light produced through illuminating with light a particle included in a gas; (b) a gas inspection flow path for introducing, into the airborne particle detecting device, a particle included in a gas that is subject to inspection; (c) a collecting mechanism for dispersing into the air, and then collecting, a particle that is adhered to a solid that is subject to inspection; (d) and a solids inspection flow path for introducing, into the airborne particle detecting device, a particle collected by the collecting mechanism.

Moreover, the present invention provides a particle detecting method, wherein: (a) a gas to be inspected is introduced into an airborne particle detecting device; and (b) an aerosol is generated from a liquid to be inspected, and the aerosol is introduced into the airborne particle detecting device, wherein: (c) in the airborne particle detecting device, a particle that is included in the gas that is subject to inspection and a particle that is included in the aerosol are illuminated with light, and scattered light and/or fluorescent light produced by the particle is detected.

The present invention provides a particle detecting system and particle detecting method wherein it is possible to detect particles sampled from a plurality of locations using a single particle detecting device.

BRIEF DESCRIPTIONS OF THE DRAWINGS

FIG. 8 is a schematic diagram of an aerosol generating portion according to the example according to the present invention.

DETAILED DESCRIPTION

Examples of the present invention will be described below. In the descriptions of the drawings below, identical or similar components are indicated by identical or similar codes. Note that the diagrams are schematic. Consequently, specific measurements should be evaluated in light of the descriptions below. Furthermore, even within these drawings there may, of course, be portions having differing dimensional relationships and proportions.

Example

Figure 1:
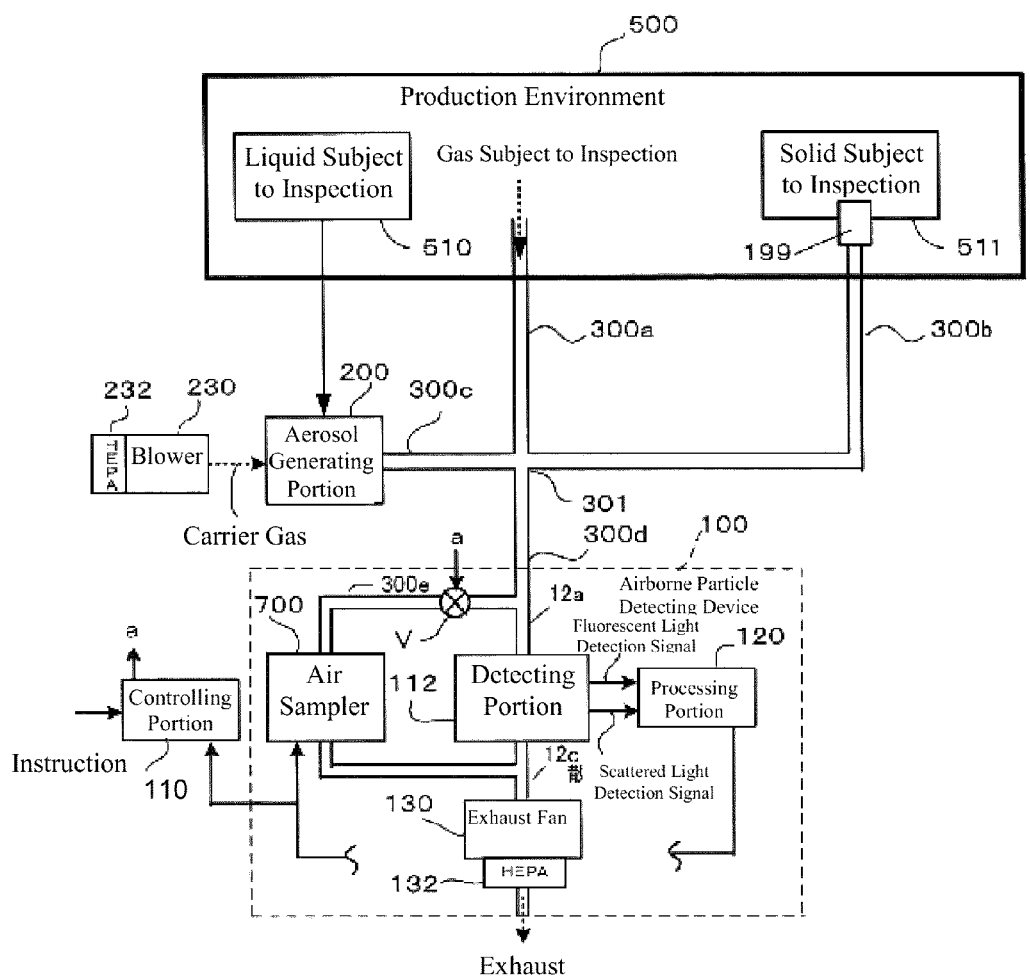
FIG. 1 is a schematic top view diagram of a particle detecting system according to an example according to the present invention.

As illustrated in FIG. 1, a particle detecting system according to an example includes: an airborne particle detecting device 100 that detects scattered light and/or fluorescent light that is produced through illuminating, with light, a particle included in a gas; a gas inspection flow path 300*a* that introduces, into an airborne particle detecting device 100, particles included in the gas that is subject to inspection; an aerosol generating portion 200 that generates an aerosol from a liquid 510 that is subject to inspection; and a liquids inspection flow path 300*c* that introduces, into the airborne particle detecting device 100, particles included in the aerosol.

The particle detecting system may further includes: a collecting mechanism 199 that disperses into the gas, and then collecting particles that are adhered to a solid 511 that is subject to inspection; and a solids inspection flow path 300*b* that introduces, into the airborne particle detecting device 100, particles captured by the collecting mechanism 199.

Figure 2:
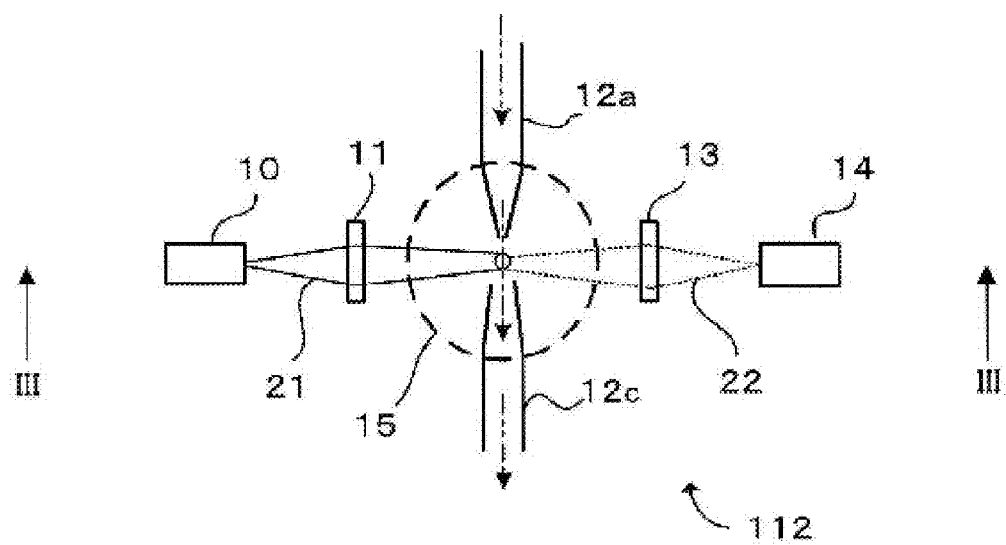
FIG. 2 is a schematic top view diagram of a detecting portion of an airborne particle detecting device according to the example according to the present invention.
Figure 3:
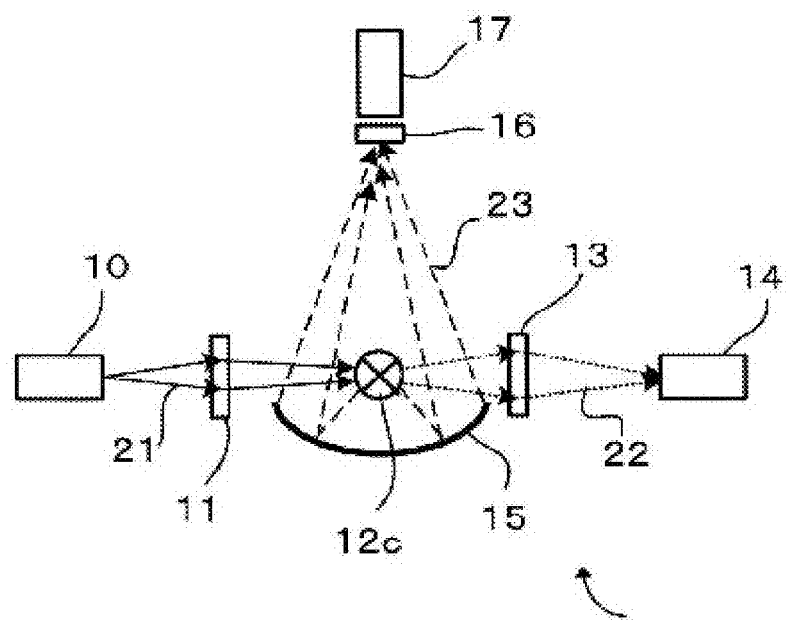
FIG. 3 is a schematic cross-sectional diagram viewed along the section III-III in FIG. 2, of the detecting portion of the airborne particle detecting device according to the example.
Figure 4:
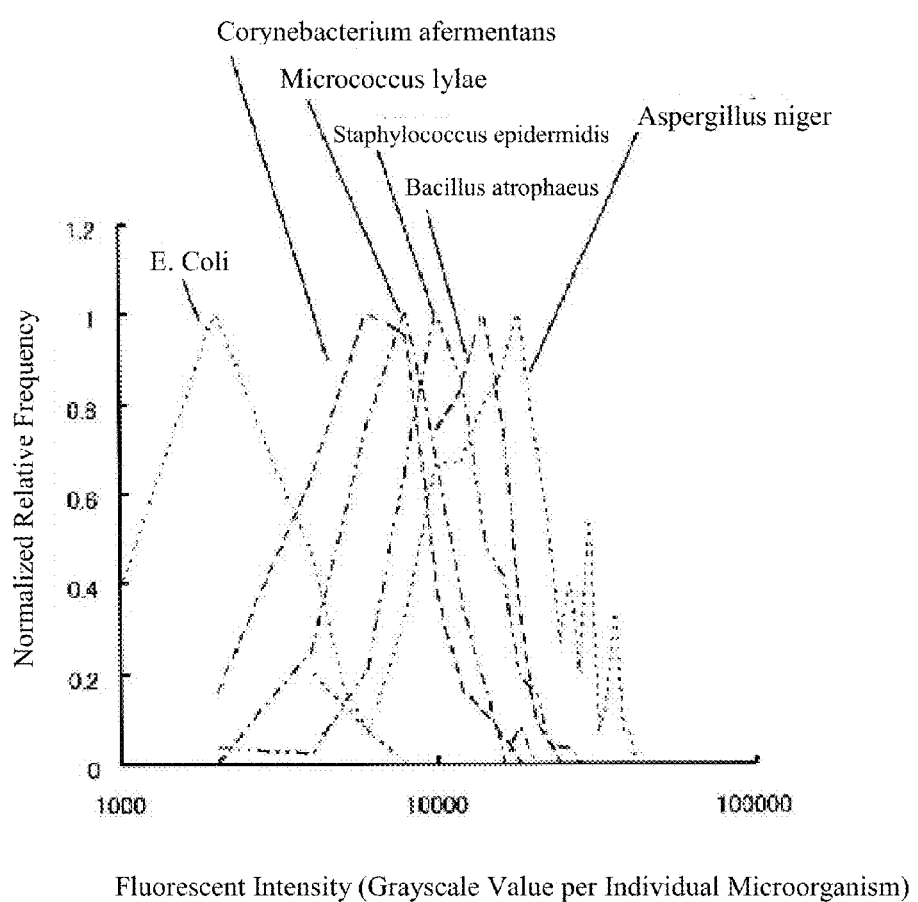
FIG. 4 is a graph illustrating the fluorescent intensities for each of various types of microorganisms in the example according to the present invention.
Figure 5:
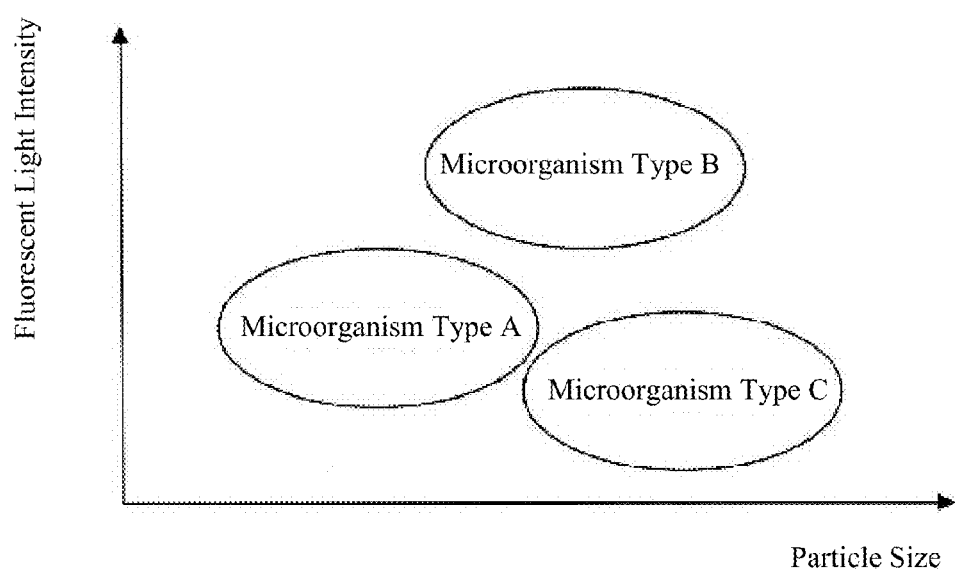
FIG. 5 is a graph illustrating schematically the relationship between the fluorescent intensity and the particle diameters of microorganisms within a liquid, in the example according to the present invention.

The airborne particle detecting device 100 is provided with a detecting portion 112. As illustrated in FIG. 2 and FIG. 3, the detecting portion 112 is provided with a light source 10, a focusing lens 11 for condensing the light that is emitted by the light source 10, a test sample flow path 12*a* that includes a nozzle for spraying a gas toward the focal point of the focusing lens 11, and a test sample flow path 12*c* into which is introduced the gas that is sprayed from the test sample flow path 12*a*.

The test sample flow path 12*a*, as illustrated in FIG. 1, is connected to a shared flow path 300*d* that is in communication with a gas inspection flow path 300*a*, a solids inspection flow path 300*b*, and a liquids inspection flow path 300*c*. Moreover, the test sample flow path 12*c* that is illustrated in FIG. 2 is connected and exhaust fan 130 that has, for example, a HEPA filter (High Efficiency Particulate Air filter) 132 that is illustrated in FIG. 1. The gas is caused to flow into the test sample flow path 12*c* from the test sample flow path 12*a*, illustrated in FIG. 2, at a constant flow rate by the exhaust fan 130 and a pressure regulator, and the like.

A solid-state laser, a gas laser, a semiconductor laser, a light-emitting diode, or the like, can be used as the light source 10. Where a particle is included in the gas that is sprayed from the test sample flow path 12*a*, the particle, when illuminated with the light, produces scattered light. The scattered light is focused by a focusing lens 13 to be detected by a scattered light detecting device 14. A photodiode, or the like, may be used as the scattered light detecting device 14. When scattered light impinges on the scattered light detecting device 14, an electrical scattered light detection signal is produced and sent to the processing portion 120, illustrated in FIG. 1. The processing portion 120 is included in, for example, a computer system. The processing portion 120 evaluates whether or not there is a particle based on whether or not there is a scattered light detection signal. Moreover, the processing portion 120 counts the number of particles based on the number of times that a scattered light detection signal has been received. Moreover, because there is a correlation between the intensity of the scattered light and the size of the particle, the processing portion 120 calculates the size, such as the diameter, of the detected particle based on the intensity of the scattered light. Moreover, if the particle is a microorganism, the particle diameter of the microorganism will be different depending on the type of microorganism. Because of this, the processing portion 120 may identify the type of microorganism from the particle diameter that is detected.

Moreover, when a fluorescent particle, such as a microorganism, is included in the gas that is sprayed from the test sample flow path 12*a*, shown in FIG. 2, the particle, when illuminated with light, will emit fluorescent light. Examples of microorganisms include microbes. Examples of such microbes include Gram-negative bacteria, Gram-positive bacteria, and fungi such as mold spores. *Escherichia coli*, for example, can be listed as an example of a Gram-negative bacterium. *Staphylococcus epidermidis, Bacillus atrophaeus, Micrococcus lylae*, and *Corynebacterium afermentans* can be listed as examples of Gram-positive bacteria. *Aspergillus niger* can be listed as an example of a fungus such as a mold spore. However, the microorganisms are not limited to these specific examples. For example, the nicotinamide adenine dinucleotide and the riboflavin, and the like, that are included in microorganisms produce fluorescent light.

The fluorescent light is focused by a focusing mirror 15 and detected by the fluorescent light detecting device 17 illustrated in FIG. 3. A filter 16 for shielding the fluorescent light detecting device 17 from the light of wavelengths other than those of the fluorescent light may be disposed in front of the fluorescent light detecting device 17. A photodiode, or the like, may be used for the fluorescent light detecting device 17. When fluorescent light impinges on the fluorescent light detecting device 17, an electrical fluorescent light detection signal is produced and sent to the processing portion 120, illustrated in FIG. 1. The processing portion 120 evaluates whether or not there is a fluorescent particle based on whether or not there is a fluorescent light detection signal. Moreover, the processing portion 120 counts the number of fluorescent particles based on the number of times that a fluorescent light detection signal has been received. Moreover, as illustrated in FIG. 4, the intensity of the fluorescent light that is produced by the microorganism will differ depending on the type of microorganism. Because of this, as illustrated in FIG. 1, the processing portion 120 may identify the type of microorganism from the fluorescent intensity that is detected.

Moreover, when, for example, the processing portion 120 detects scattered light and fluorescent light, it may evaluate the detected particle as a microorganism particle. Moreover, when the processing portion 120 detects scattered light but does not detect fluorescent light, it may evaluate the detected particle as a non-microorganism particle. Moreover, the processing portion 120, although not limited thereto, may identify the type of microorganism based on both the fluorescent light intensity and the scattered light intensity following the method described in U.S. Pat. No. 6,885,440 and U.S. Pat. No. 7,106,442. For example, as illustrated in FIG. 5, correlations can be seen with the particle diameters and fluorescent intensities depending on the type of microorganism. Consequently, it is possible to identify the type of microorganism from the fluorescent intensity and the particle diameter through obtaining in advance a graph such as illustrated in FIG. 5.

The airborne particle detecting device 100 may also identify the type of microorganism by detecting the microorganism through scattered light alone, without detecting fluorescent light. It is possible to identify the type of microorganism through a statistical method such as, for example, the support vector machine (SVM) method by using concentric circular scattered light detecting devices and calculating the scattered light intensity for individual angles. (See, for example, Murugesan Venkatapathi et al., "High-speed Classification of Individual Bacterial Cells Using a Model-based Light Scatter System and Multivariate Statistics," Applied Optics, USA, Optical Society of America, Feb. 10, 2008, Vol. v47, No. 5, pp. 678 through 686.)

Conversely, the airborne particle detecting device 100 may detect the fluorescent spectrum when excitation beams of a plurality of wavelengths are directed toward the gas. For example, it is possible to identify a microorganism based on the detection of the fluorescent spectrum at wavelengths of 350 nm, 450 nm, and 550 nm, when a microorganism is illuminated with an excitation beam with wavelengths of 266 nm and 355. (See, for example, Vasanthi Sivaprakasam et al., "Multiple UV Wavelength Excitation and Fluorescence of Bioaerosols," Optics Express, USA, Optical Society of America, Sep. 20, 2004, Vol. 12, No. 19, pp. 4457 through 4466.)

The gas inspection flow path 300a, illustrated in FIG. 1, has the inlet opening thereof disposed in a production environment 500. The production environment 500 may be, for example, a clean room. A manufacturing line, for example, is disposed in the production environment 500. The manufacturing line is a manufacturing line, for, for example, precision instruments, electronic components, or semiconductor devices. Conversely, the manufacturing line may be a manufacturing line for foodstuffs, beverages, or pharmaceuticals. For example, in the manufacturing line an infusion liquid may be filled into an intravenous infusion device or a hypodermic before shipping. Conversely, the manufacturing line may manufacture oral medications or Chinese herb medications. On the other hand, the manufacturing line may fill containers with a vitamin drink or beer.

Moreover, the work of culturing and preparing cultured tissues used in regenerative treatments, the handling of highly active pharmaceuticals such as antibody drugs, or the like, breeding of immunodeficient mice, and sterility limit testing for pharmaceuticals, and the like, may be performed in such a production environment 500.

A manufacturing line that is disposed in such a production environment 500 normally is controlled so that microorganisms and non-microorganism particles, and the like, are not dispersed into the air within the clean room. However, a manufacturing line, for some reason, is a source that produces microorganisms and non-microorganism particles that become airborne in the clean room. Moreover, factors other than the manufacturing line also disperse microorganisms and non-microorganism particles into the air of the clean room.

The gas inspection flow path 300a is connected to a shared flow path 300d through a branched coupling 301, and is also connected to a test sample flow path 12a of the airborne particle detecting device 100. The gas that is subject to inspection in the production environment 500 is drawn in from an inlet opening of the gas inspection flow path 300a by an exhaust fan 130, and passes through a branched coupling 301 and the shared flow path 300d, to be conveyed to the detecting portion 112 of the airborne particle detecting device 100. When there are particles in the gas that is subject to inspection, scattered light and/or fluorescent light is detected by the airborne particle detecting device 100. Note that when the air pressure in the production environment 500 is higher than the air pressure of the detecting portion 112 of the airborne particle detecting device 100, the particles included in the gas that is subject to inspection can be conveyed to the detecting portion 112 of the airborne particle detecting device 100 without the use of the exhaust fan 130.

Figure 6:
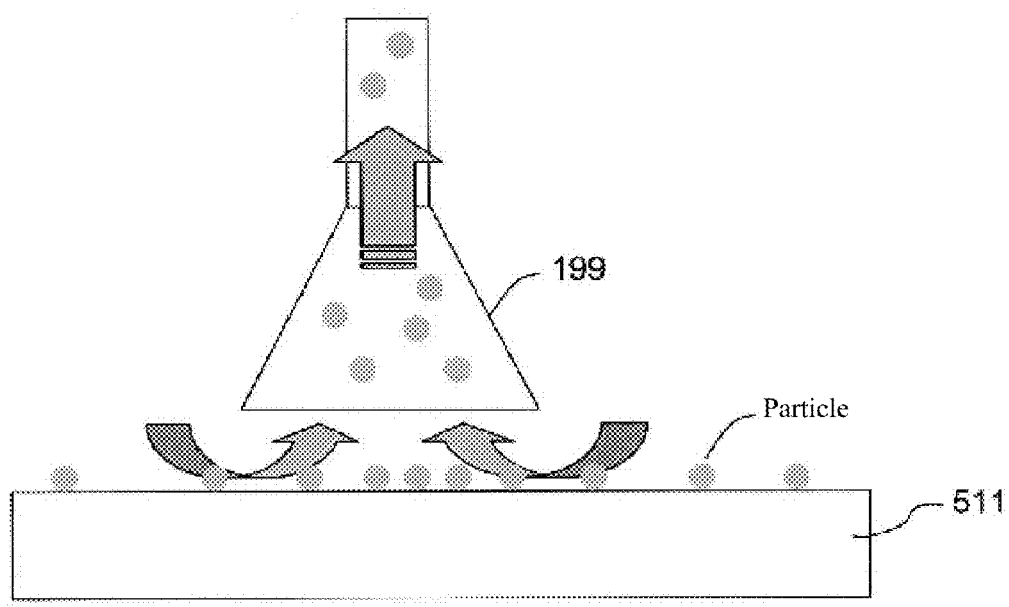
FIG. 6 is a schematic diagram of a collecting mechanism according to the example according to the present invention.
Figure 7:
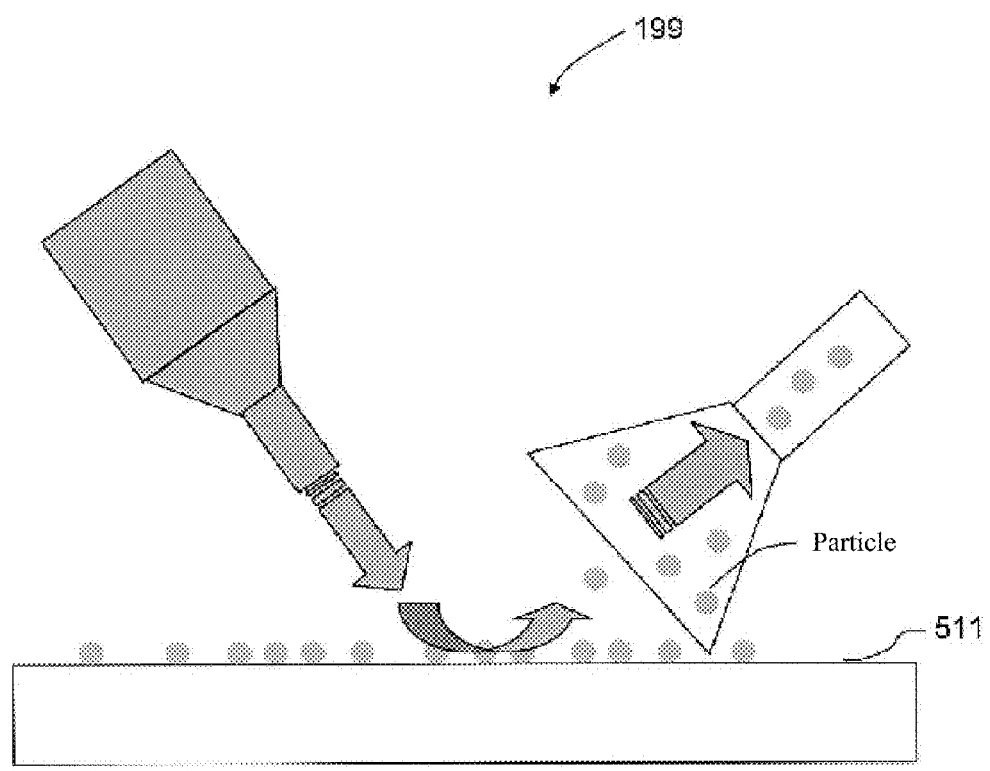
FIG. 7 is a schematic diagram of a collecting mechanism according to the example according to the present invention.

Moreover, solids 511 subject to inspection, such as biosafety cabinets, clean benches, manufacturing line equipment, walls, floors, and the like, which should be inspected for whether or not there are adhered particles, exist within the production environment 500. The collecting mechanism 199 disperses into the air the particles that are adhered to the solids 511 that are subject to inspection, and collects the particles that are scattered into the air. The collecting mechanism 199, as illustrated in FIG. 6, for example, is provided with a suction nozzle for drawing in particles that are adhered to the solid 511 that is subject to inspection. Conversely, the collecting mechanism 199, as illustrated in FIG. 7, may be provided with a jet nozzle for blow into the air the particles that are adhered to the solid 511 that is subject to inspection, and a suction nozzle for drawing in the particles that have been blown into the air.

The solids inspection flow path 300b for introducing, into the airborne particle detecting device 100 that is illustrated in FIG. 1, particles that are collected by the collecting mechanism 199 is connected through the branched coupling 301 to the shared flow path 300d, and further is connected to the test sample flow path 12a of the airborne particle detecting device 100. The particles collected from the surface of the solid 511 that is subject to inspection are caused, by the exhaust fan 130 to pass through the solids inspection flow path 300b, the branched coupling 301, and the shared flow path 300d, to be conveyed to the detecting portion 112 of the airborne particle detecting device 100. When particles are collected from the surface of the solid 511 that is subject to inspection, scattered light and/or fluorescent light is detected by the airborne particle detecting device 100. Note to that when the collecting mechanism 199 has a suction device, the particles may be conveyed to the detecting portion 112 of the airborne particle detecting device 100 without the use of the exhaust fan 130.

Moreover, in the production environment 500 there are liquids 510 that are subject to inspection, to inspect whether or not they include particles. The liquid 510 that is subject to inspection is supplied to an aerosol generating portion 200 through a pipe, or the like. The aerosol generating portion 200 nebulizes the liquid 510 that is subject to inspection, to produce an aerosol of a dispersion system wherein the dispersed phase is solid or liquid, with air as the dispersing medium.

Figure 8:
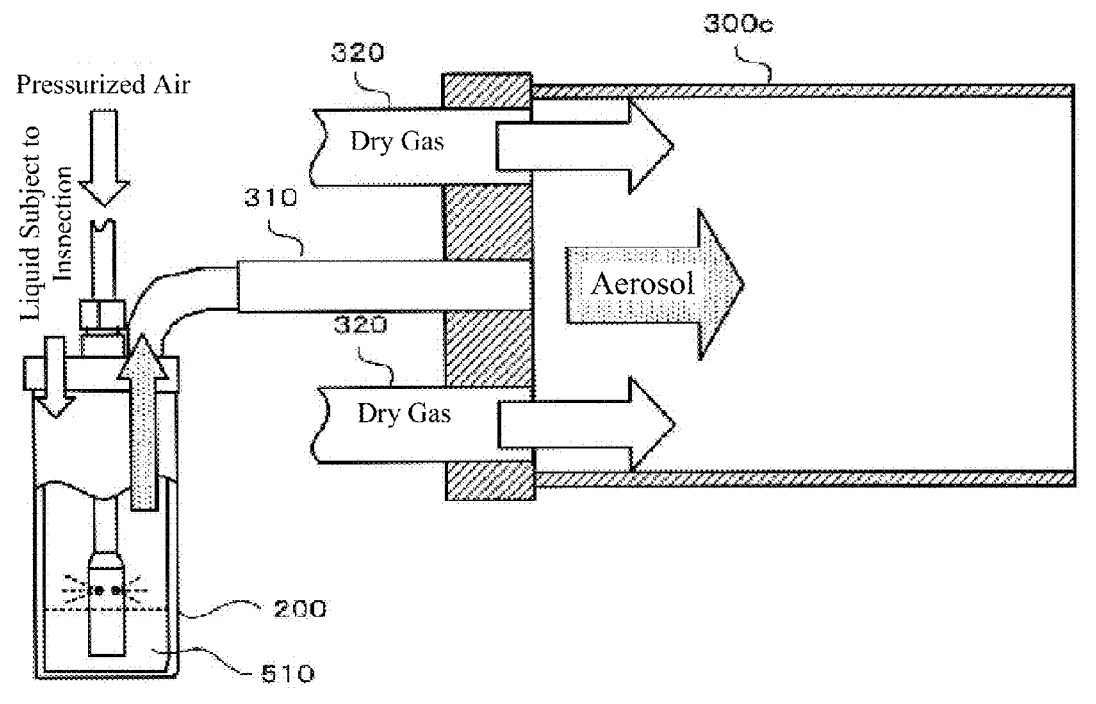

A nebulizer or, more specifically, a collision nebulizer such as shown in FIG. 8, can be used as the aerosol generating portion 200. A collision nebulizer forces the liquid 510 that is subject to inspection into a capillary tube, and then sprays the liquid 510 that is subject to inspection against a container wall face from a jet nozzle that is provided on the capillary tube, to generate an aerosol. The aerosol that is generated is introduced into the liquids inspection flow path 300c through a pipe 310, or the like. Pressurized or compressed air is blown from a blowing fan 230 that has a HEPA filter 232, or the like, shown in FIG. 1. The pressure of the pressurized or compressed air can be adjusted to adjust the flow rate of the aerosol. Moreover, the higher the pressure, the finer the diameters of the droplets included in the aerosol.

As illustrated in FIG. 8, a plurality of inlet holes is provided in a circle on an end portion sidewall of the liquids inspection flow path 300c, and a dry gas 320 is introduced through this plurality of inlet holes. In this case, the dry gas 320 flows along the inner walls of the liquids inspection flow path 300c. The aerosol is mixed with the dry gas 320 in the liquids inspection flow path 300c, and the dispersion phase of the liquid, such as droplets, etc., produces vapor. The dry gas 320 also functions as a carrier gas for the microorganisms or solid non-microorganism particles, or the like, that are included in a solid dispersion phase in the aerosol. The dry gas 320 may be air, or may be an inert gas, such as nitrogen gas, in order to prevent a chemical reaction with the aerosol. Moreover, a baffle plate may be provided in the liquids inspection flow path 300c, to prevent adhesion of the particles in the liquids inspection flow path 300c.

As illustrated in FIG. 1, the liquids inspection flow path 300c is connected to a shared flow path 300d through a branching coupling 301, and is also connected to a test sample flow path 12a of the airborne particle detecting device 100. The aerosol that is generated by the aerosol generating portion 200 is drawn in from an inlet opening of the liquids inspection flow path 300c by an exhaust fan 130, and passes through a branched coupling 301 and the shared flow path 300d, to be conveyed to the detecting portion 112 of the airborne particle detecting device 100. When there are particles in the aerosol, scattered light and/or fluorescent light is detected by the airborne particle detecting device 100. Note to that the particles included in the aerosol may be conveyed to the detecting portion 112 of the airborne particle detecting device 100 without the use of the exhaust fan 130 through a blowing fan 230, for example, alone.

Moreover, a bypass flow path 300e that bypasses the detecting portion 112 from the shared flow path 300d may be provided connecting to the exhaust fan 130, a valve V that is opened and closed by an opening/closing signal a, and an air sampler 700 that is provided with a membrane filter, or the like, for collecting microorganisms may be provided in the bypass flow path 300e. When the detecting portion 112 detects a microorganism, the valve V is opened to guide the microorganisms within the shared flow path 300d to the air sampler 700, making it possible to collect the microorganisms that were included in the gas that is subject to inspection or the liquid that is subject to inspection. This makes it possible to culture, on a culturing medium, the microorganisms that were collected, to produce colonies, enabling observations thereof with either the naked eye or under a microscope, or to perform image processing on a photograph taken of the colony, to enable high precision identification of the type of microorganism. The valve V is connected electrically to a controlling portion 110. The controlling portion 110 sends the opening/closing signal a to the valve V.

The gas inspection flow path 300a, the solids inspection flow path 300b, the liquids inspection flow path 300c, the shared flow path 300d, and the bypass flow path 300e are pipes made out of metal, such as stainless steel, and while it may be a sanitary pipe with the surface thereof polished, there is no limitation thereto. A diaphragm valve that opens and closes the flow path through vertical motion of a diaphragm, a ball valve of a revolving handle type that opens and closes the flow path through rotating the revolving handle, a ball valve of the gear handle type that opens and closes the flow path using a gear handle, a butterfly valve for opening and closing the flow path by rotating a disk using the stem as the axis, or the like, may be used for the valve V. Moreover, the valve V may be actuated by an electrically driven motor, an electromagnetic force, air pressure, or the like.

The particle detecting system according to the example, explained above, is able to detect particles included in a gas that is subject to inspection, particles adhered to a solid that is subject to inspection, and particles that are included in a liquid that is subject to inspection as well, through a single airborne particle detecting device 100.

Another Example

A cloth may be used to wipe particles from the surface of a solid 511 that is subject to inspection, and the cloth may be shaken near the inlet of the gas inspection flow path 300a, to disperse the particles from the cloth to detect, using the airborne particle detecting device 100, particles deriving from the surface of the solid 511 that is being inspected. Conversely, a swab, or the like, may be used to wipe up particles from the surface of the solid 511 that is subject to inspection, and the swab may be submerged in distilled water to disperse the particles into the distilled water, to produce a liquid 510 to be subjected to inspection. This can also inspect for whether or not there are particles adhered to the surface of the solid 511 that is subject to inspection.

Yet Another Example

Figure 9:
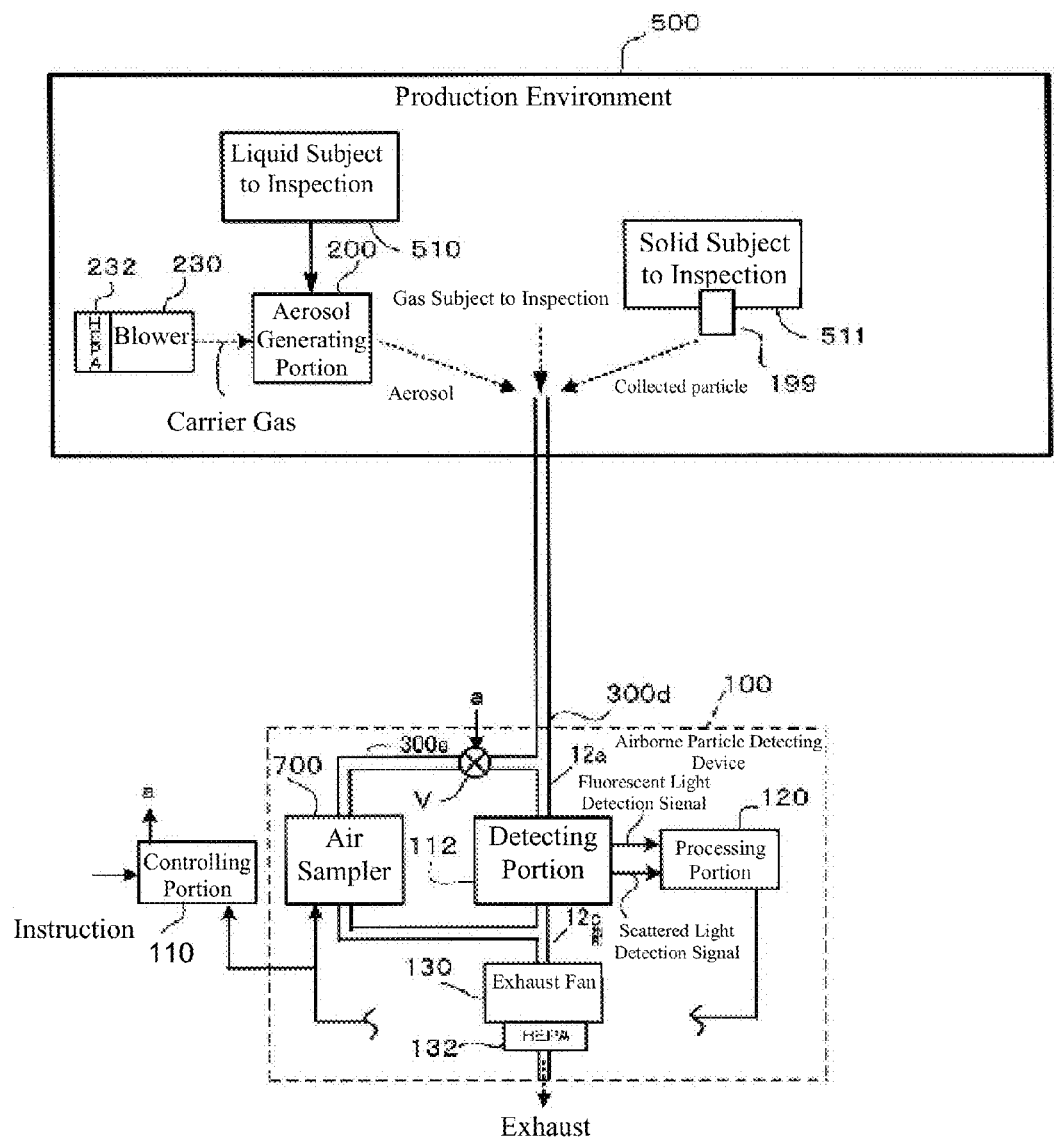
FIG. 9 is a schematic top view diagram of a particle detecting system according to yet another example according to the present invention.

As discussed above, the example illustrated in FIG. 1 describes the particle detecting system wherein a gas that is subject to inspection is introduced into an airborne particle detecting device 100 by a gas inspection flow path 300a, and particles included in an aerosol were introduced into an airborne particle detecting device 100 by a liquids inspection flow path 300c, and particles collected by a collecting mechanism 199 are introduced into the airborne particle detecting device 100 through a solids inspection flow path 300b. In contrast, as illustrated in FIG. 9, an inlet of the shared flow path 300d may be disposed in the production environment 500, and the particles included in the gas that is subject to inspection, the particles included in the aerosol, and the particles collected by the collecting mechanism 199 may be introduced directly into the inlet of the shared flow path 300d.

Other Examples

While there are descriptions of the examples as set forth above, the descriptions and drawings that form a portion of the disclosure are not to be understood to limit the present invention. A variety of alternate examples and operating technologies should be obvious to those skilled in the art. For example, while in one or more of the examples the explanation was that a collision nebulizer may be used as the aerosol generating portion 200, a jet nebulizer, an ultrasonic nebulizer, a piezo element nebulizer, a centrifuge separation nebulizer, a two-fluid nozzle, a mini atomizer nozzle, or the like, may be used instead.

A jet nebulizer draws up the liquid to the nozzle through the capillary phenomenon, and sprays it together with air to produce a mist, where the mist is mixed with dry gas to produce an aerosol. The higher the gas pressure, the finer the diameters of the particles that are included in the mist. The amount of the aerosol may be adjusted through varying the amount of mist produced, and the flow rate of the dry gas.

An ultrasonic nebulizer produces droplets or a mist through an ultrasonic vibrator, where the droplets or mist is mixed with the dry gas to produce an aerosol. The amount of the aerosol may be adjusted through varying the amount of droplets or mist produced, and the flow rate of the dry gas.

A piezo element nebulizer produces droplets through a piezo element, where the droplets or mist is mixed with the dry gas to produce an aerosol. The amount of the aerosol may be adjusted through varying the amount of droplets produced, and the flow rate of the dry gas.

A centrifugal separation nebulizer sprays a solution onto a rotating disk, and the solution is thrown off of the disk to produce produces droplets, where the droplets are mixed with dry gas to produce an aerosol. The amount of the aerosol may be adjusted through varying the speed of rotation of the rotating disk, and the flow rate of the dry gas.

In a two-fluid nozzle, a liquid and air are mixed simultaneously within a pipe to nebulize a mist that includes ultrasmall particles. The amount of the liquid and the amount of the air that are mixed can be adjusted through the respective pressures thereof. The greater the amount of air relative to the amount of liquid in the mixture tends to cause the diameters of the droplets to be smaller. Moreover, the two-fluid nozzle can also be autoclavable.

A mini atomizer nozzle produces an aerosol through producing a mist within the pipe and mixing the mist with a dry gas. The droplets included in the mist that is generated by the mini atomizer nozzle tend to be small, and increasing the size of the spray opening tends to reduce the likelihood of blockages. Moreover, the mini atomizer nozzle can also draw in and nebulize high viscosity liquids. Moreover, the mini atomizer nozzle can also be autoclavable.

Moreover, the gas inspection flow path 300a, illustrated in FIG. 1, may be disposed so as to be able to draw in gas from within a biosafety cabinet or a clean bench. Furthermore, the liquids inspection flow path 300c may be disposed so as to draw in an aerosol produced from a culture liquid in a culture dish that is placed within a biosafety cabinet or clean bench. In this way, the present invention should be understood to include a variety of examples, and the like, not set forth herein.

The invention claimed is:

1. A particle detecting system comprising:
    an airborne particle detecting device that detects scattered light and/or fluorescent light produced through illuminating with light a particle included in a gas;
    a gas inspection flow path that introduces, into the airborne particle detecting device, a particle included in a gas that is subject to inspection;
    an aerosol generating portion that generates an aerosol from a liquid that is subject to inspection;
    a liquids inspection flow path that introduces, into the airborne particle detecting device, a particle included in the aerosol; and
    an inlet that introduces a dry gas into the said liquids inspection flow path.

2. The particle detecting system as set forth in claim 1, further comprising:
    a collecting mechanism that disperses into the air, and then collects, a particle that is adhered to a solid that is subject to inspection; and
    a solids inspection flow path that introduces, into the airborne particle detecting device, a particle collected by the collecting mechanism.

3. A particle detecting system comprising:
    an airborne particle detecting device that detects scattered light and/or fluorescent light produced through illuminating with light a particle included in a gas;
    a gas inspection flow path that introduces, into the airborne particle detecting device, a particle included in a gas that is subject to inspection;
    a collecting mechanism that disperses into the air, and then collects, a particle that is adhered to a solid that is subject to inspection;
    a solids inspection flow path that introduces, into the airborne particle detecting device, a particle collected by the collecting mechanism; and
    a suction nozzle provided with the collecting mechanism.

4. The particle detecting system as set forth in claim 3, further comprising:
    an aerosol generating portion that generates an aerosol from a liquid that is subject to inspection; and
    a liquids inspection flow path that introduces, into the airborne particle detecting device, a particle included in the aerosol.

5. The particle detecting system as set forth in claim 2, wherein:
    the collecting mechanism comprises a suction nozzle that draws in the particle.

6. The particle detecting system as set forth in claim 2, wherein:
    the collecting mechanism comprises a jet nozzle that blows into the air a particle that is adhered to the solid that is subject to inspection.

7. A particle detecting method comprising:
    introducing a gas to be inspected into an airborne particle detecting device;
    generating an aerosol from a liquid to be inspected; and
    introducing the aerosol and a dry gas into the airborne particle detecting device, wherein:
    in the airborne particle detecting device, a particle that is included in the gas that is subject to inspection and a particle that is included in the aerosol are illuminated with light, and scattered light and/or fluorescent light produced by the particle is detected.

8. The particle detecting method as set forth in claim 7, further comprising:
    dispersing a particle, which is adhered to a solid that is subject to inspection, into the air;
    collecting the particle; and
    introducing the particles that have been collected into an airborne particle detecting device, wherein:
    in the airborne particle detecting device, a particle that is included in the gas that is subject to inspection, a particle that is included in the aerosol, and a particle collected from the solid that is subject to inspection, are illuminated with light, and scattered light and/or fluorescent light produced by the particles is detected.

9. The particle detecting method as set forth in claim 8, wherein:
    in the collecting, a particle is drawn in by a suction nozzle.

10. The particle detecting method as set forth in claim 8, wherein:
    in the collecting, the particle that is adhered to the solid subject to inspection is blown into the air by a jet nozzle.

* * * * *